(12) United States Patent
Nishiura (10) Patent No.: US 10,020,719 B2
(45) Date of Patent: Jul. 10, 2018

(54) LINEAR ACTUATOR (71) Applicant: SUNSTAR INC., Takatsuki-shi, Osaka (JP)

(72) Inventor: Masahiro Nishiura, Takatsuki (JP)

(73) Assignee: SUNSTAR INC., Osaka (JP)

( * ) Notice: Subject to any disclaimer, the term of this patent is extended or adjusted under 35 U.S.C. 154(b) by 348 days.

(21) Appl. No.: 14/736,681

(22) Filed: Jun. 11, 2015

(65) Prior Publication Data
US 2015/0280537 A1 Oct. 1, 2015

Related U.S. Application Data (62) Division of application No. 13/133,606, filed as application No. PCT/JP2009/070339 on Dec. 3, 2009, now Pat. No. 9,072,576.

(30) Foreign Application Priority Data

Dec. 8, 2008 (JP) .................................. 2008-312099

(51) Int. Cl.
*H02K 33/16* (2006.01)
*H02K 33/12* (2006.01)
(Continued)

(52) U.S. Cl.
CPC ......... *H02K 33/12* (2013.01); *A61C 17/3445* (2013.01); *H02K 33/02* (2013.01); *H02K 16/00* (2013.01)

(58) Field of Classification Search
CPC ........ H02K 33/02; H02K 33/04; H02K 33/06; H02K 33/08; H02K 33/16; H02K 35/02;
(Continued)

(56) References Cited

U.S. PATENT DOCUMENTS 3,103,603 A * 9/1963 Reutter ................. H02K 33/06
310/15
3,149,255 A * 9/1964 Trench .................. H02K 33/06
310/30
(Continued)

FOREIGN PATENT DOCUMENTS

JP 09-205763 A 8/1997
JP 11-019589 A 1/1999
(Continued)

OTHER PUBLICATIONS

International Search Report for PCT/JP2009/070339, dated Feb. 23, 2010.

*Primary Examiner* — Tran Nguyen
(74) *Attorney, Agent, or Firm* — Westerman, Hattori, Daniels & Adrian, LLP (57) ABSTRACT

Provided is a linear actuator which is simple in structure, inexpensive to manufacture, in addition, has small magnetic leakage, and can provide a large inertial force without increasing the number of parts and weight. The linear actuator is provided with an output shaft 12 which is supported on a supporting case 11 so as to linearly reciprocate freely, an elastic member 13 which biases the output shaft 12 toward a middle position of the linear reciprocation thereof, a permanent magnet 14 which is fixed to the output shaft 12, a coil 15 which linearly reciprocates the output shaft 12 by having a variable magnetic field act on the permanent magnet 14 and is fixed to the supporting case 11 such that the coil 15 faces one of magnetic poles of the permanent magnet 14, a yoke 16, which is composed of a magnetic material, has a midway portion tightly secured to the other magnetic pole of the permanent magnet 14, extends to the exterior of the coil 15 along the exterior of the permanent magnet 14 with a space from the permanent magnet 14, and has an end portion disposed close to the
(Continued)

exterior of the coil 15, and power supply means for forming a variable magnetic field on the coil 15.

4 Claims, 8 Drawing Sheets

(51) Int. Cl.
*A61C 17/34* (2006.01)
*H02K 33/02* (2006.01)
*H02K 16/00* (2006.01)

(58) Field of Classification Search
CPC ....... H02K 41/00; H04R 11/02; H02P 25/032; A61C 17/00; A61C 17/16; A61C 17/22; A61C 17/34; A61C 17/3445; A61N 1/32; A61N 1/322; B06B 1/0215; B06B 1/045; B26B 19/28; B26B 19/282; F16F 7/10; F16F 7/104

See application file for complete search history.

(56) References Cited

U.S. PATENT DOCUMENTS

| | | | | |
|---|---|---|---|---|
| 3,577,579 | A * | 5/1971 | Duve | A61C 17/3472 15/22.1 |
| 4,928,028 | A * | 5/1990 | Leibovich | H01F 7/1646 310/23 |
| 6,873,067 | B2 * | 3/2005 | Ichii | A61C 17/34 310/15 |
| 7,023,112 | B2 | 4/2006 | Miyamoto et al. | |
| 7,288,863 | B2 * | 10/2007 | Kraus | B26B 19/282 310/37 |
| 2003/0142845 | A1 | 7/2003 | Miyamoto et al. | |
| 2003/0205941 | A1 | 11/2003 | Suzuki et al. | |
| 2004/0010871 | A1 | 1/2004 | Nishinaka et al. | |
| 2007/0011834 | A1 | 1/2007 | Shimizu et al. | |
| 2007/0040457 | A1 | 2/2007 | Shimizu et al. | |
| 2008/0258566 | A1 | 10/2008 | Shimizu et al. | |

FOREIGN PATENT DOCUMENTS

| | | |
|---|---|---|
| JP | 2001-339931 A | 12/2001 |
| JP | 2002-176758 A | 6/2002 |
| JP | 2003-14022 A | 1/2003 |
| JP | 2003-80171 A | 3/2003 |
| JP | 2003-220363 A | 8/2003 |
| JP | 2004-343931 A | 12/2004 |

* cited by examiner

FIG. 9

LINEAR ACTUATOR

CROSS-REFERENCE TO RELATED APPLICATIONS

This application is a Divisional of U.S. application Ser. No. 13/133,606, filed Jun. 8, 2011, and wherein application Ser. No. 13/133,606 is a national stage application filed under 35 USC § 371 of International Application No. PCT/JP2009/070339, filed Dec. 3, 2009, and which is based upon and claims the benefit of priority from the prior Japanese Patent Application No. 2008-312099, filed on Dec. 8, 2008, the entire contents of which are incorporated herein by reference.

TECHNICAL FIELD

The present invention relates to a linear actuator which can be preferably utilized as driving means for various devices provided with an actuating portion which linearly reciprocates such as an electric toothbrush, an electric gum massager, an electric shaver, an electric pump and the like.

BACKGROUND ART

Such electric toothbrushes have widely been put to practical use as one which linearly reciprocates a cleaning head having a plurality of bristle bundles implanted therein in a direction generally perpendicular to an implanted direction of the bristle bundles, one which inversionally reciprocate the cleaning head around the implanted direction of the bristle bundles, one which vibrates the cleaning head together with a casing, and the like. In this regard, the inversional reciprocation in this specification indicates a movement which repeatedly carries out such a rotational movement that the cleaning head rotates a certain degree of angle in a forward direction and then rotates the same degree of angle in a reverse direction.

Further, as driving means of the electric toothbrush which linearly reciprocates the cleaning head, driving means which is provided with a converting means such as a crank mechanism for converting a rotational movement of a rotational shaft of a motor to a linear reciprocation of an output shaft is widely employed because of its low manufacturing cost. However, since a vibrational frequency of the cleaning head is limited when it is linearly reciprocated by a motor, an electric toothbrush which uses a linear actuator having a permanent magnet and a coil has also been put to practical use recently in order to improve a cleaning efficiency by increasing the vibrational frequency of the cleaning head.

As for the electric toothbrush using the linear actuator, there has been proposed one which is provided with a plunger supported so as to reciprocate freely in an axis direction thereof, a spring member which uses a moving part including the plunger as a vibration system, electromagnetic driving means for driving the moving part so as to reciprocate at its resonance frequency when an alternating current is applied thereto, and restricting means for restricting a rotation of the moving part around an axis thereof (see Patent Document 1, for example).

Further, there has also been proposed an electric toothbrush which is provided with a shaft supported so as to linearly reciprocate freely in an axis direction thereof and tubular permanent magnets each having a central axis generally coincident with a central axis of the shaft and both end surface portions each having opposite polarity so that a moving member is constituted by the shaft and the permanent magnets, wherein the moving member is inserted into a tubular stator provided with a winding so as to linearly reciprocate freely and the moving member is reciprocated by applying current to the winding (See Patent Document 2, for example).

Patent Document 1: Japanese Patent Laid-Open Publication No. 2002-176758
Patent Document 2: Japanese Patent Laid-Open Publication No. 2004-343931

SUMMARY OF INVENTION

Technical Problem

In the electric toothbrush described in Patent Document 1, since the coil and the permanent magnets are provided inside a casing with generally no space from an inner surface of the casing, there is a concern of an adverse effect on another device such as a pacemaker caused by magnetic leakage to the outside of the casing. Accordingly, it is necessary to place the coil and the permanent magnets inside a shield case composed of a magnetic material, thereby causing such problems that a manufacturing cost of the electric toothbrush becomes higher and handleability of the electric toothbrush is deteriorated by an increased weight of the electric toothbrush due to the provision of the shield case. In addition to this, the electric toothbrush described in Patent Document 1 is complicated in structure, expensive to manufacture, and in addition, has sort of bad assemblability because it needs at least two magnets to be provided. Further, there is also such a problem that a sufficient inertial force of reciprocation cannot be ensured because a lightweight shaft is reciprocated therein, as a result of which a sufficient brushing force cannot be obtained.

On the other hand, since the permanent magnets are fixed to the shaft which linearly reciprocates together with a cleaning head in the electric toothbrush described in Patent Document 2, it is possible for the permanent magnets to have functions to generate a driving force and also as a weight. Therefore, it is possible to increase the inertial force of the shaft and thereby set a brushing force to be higher without increasing the number of parts and weight. However, since a coil is disposed inside a casing with generally no space therebetween, it is necessary to place the coil inside the shield case as with the invention described in Patent Document 1. As a result, there are such problems that a manufacturing cost of the electric toothbrush becomes higher and handleability of the electric toothbrush is deteriorated by an increased weight of the electric toothbrush due to the provision of the shield case.

It is an object of the present invention to provide a linear actuator which is simple in structure, inexpensive to manufacture, in addition, has small magnetic leakage, and can provide a large inertial force without increasing the number of parts and weight.

Solution to Problem

A linear actuator according to the present invention is provided with an output member which is supported on a fixing-side member so as to linearly reciprocate freely, an elastic member which biases the output member to a middle position of the linear reciprocation, a permanent magnet which is fixed to the output member, a coil which linearly reciprocates the output member by having a variable magnetic field act on the permanent magnet and is fixed to the fixing-side member such that the coil faces one of magnetic poles of the permanent magnet, a yoke which is composed of a magnetic material, has a midway portion tightly secured to the other magnetic pole of the permanent magnet, extends to the exterior of the coil along the exterior of the permanent magnet with a space from the permanent magnet, and has an end portion disposed close to the exterior of the coil, and power supply means for forming a variable magnetic field on the coil. The yoke may be provided so as to surround generally whole outer surfaces of the permanent magnet and the coil. This makes it possible to prevent magnetic leakage from the permanent magnet and the coil to the outside more effectively. Further, an end portion of the yoke may also be located within a range from one end portion to the other end portion of the coil (namely, from one opening to the other opening of the coil). In this range, it is preferred that the end portion of the yoke is located between a central portion of the length of the coil in a centerline direction (the winding length of the coil) and the end portion of the coil at a side farther than the permanent magnet. As a result of this, it is possible to utilize a magnetic flux (magnetic force) formed by the yoke efficiently.

In this linear actuator, it is possible to form a magnetic circuit from the magnetic pole of the permanent magnet which does not face the coil to the coil by means of the yoke by tightly fixing the midway portion of the yoke to the magnetic pole of the permanent magnet which does not face the coil and disposing the end portion of the yoke close to the exterior of the coil. Therefore, the magnetic leakage of the permanent magnet can be reduced, thereby making it possible to improve a magnetic efficiency of the linear actuator. The midway portion refers to an inner bottom portion of the yoke having a bottomed tubular shape with an opening portion, namely a pot-like shape. Further, since the yoke serves as a magnetic shield for the coil and permanent magnet, it is possible to reduce the magnetic leakage from the coil and the permanent magnet to the outside without increasing the number of parts and thereby prevent an adverse effect on another device caused by the magnetic leakage before it occurs. Furthermore, it is possible to have the permanent magnet serve as a weight for increasing an inertial force of the output member because the permanent magnet is fixed to the output member. As a result of this, it is possible to increase an inertial force of the output member without increasing the number of parts and weight. Therefore, in a case where this linear actuator is used as driving means for linearly reciprocating a cleaning head of an electric toothbrush, for example, it becomes possible to increase a brushing force by the cleaning head without increasing the number of parts and weight.

In this regard, it is a preferred embodiment that a plurality of the permanent magnets are provided in the output member with a space between each of the permanent magnets and a plurality of the coils are provided corresponding to the plurality of the permanent magnets so that the plurality of the coils are synchronously driven by the power supply means. In this case, a driving force of the output member can be increased by increasing the number of the permanent magnets and the coils. Further, plural pairs of the permanent magnets and the coils may be arranged in parallel or also in series.

It is also preferred that a pair of the permanent magnets are provided in the output member with a space between each of the permanent magnets so as to be coaxial with the output member and a pair of the coils are provided corresponding to the pair of the permanent magnets so as to be coaxial with the output member so that the pair of the coils are synchronously driven by the power supply means. In this case, it is possible to increase the driving force of the output member by providing the pair of the permanent magnets and the pair of the coils without making a size of the linear actuator in a radial direction of the output member larger. For example, an electric toothbrush needs to be configured so as to have such a size that it is easily grasped by hand. Since it is possible to increase the driving force of the output member without making the size of the linear actuator in the radial direction of the output member larger in the present invention, a sufficient brushing force can be ensured while handleability of the electric toothbrush can be improved.

Further, it is also possible that a magnetic path forming member is tightly secured to one of the magnetic poles of the permanent magnet and the magnetic path forming member is disposed in a generally central portion of a circular coil so as to be close to the circular coil. By configuring the linear actuator in this manner, it becomes possible to reduce magnetic leakage in the magnetic circuit from the one of the magnetic poles of the permanent magnet to the coil, thereby further improving a magnetic efficiency of the linear actuator. The magnetic path forming member is composed of a magnetic material such as an iron material, a silicon steel plate, ferrite or the like and it is desirable to use the iron material among these materials.

Furthermore, it is also possible that the output member is elastically supported by the elastic member with respect to the fixing-side member such that the output member is inversionally reciprocated by the linear reciprocation of the output member. In this case, it is possible to inversionally reciprocate the output member with a simple structure and little waste of driving force. For example, the cleaning head can be inversionally reciprocated around a direction perpendicular to an implanted direction of bristle bundles while it is also linearly reciprocated in the direction perpendicular to the implanted direction of the bristle bundles in an electric toothbrush. This is desirable for improving a cleaning efficiency to clean a surface of tooth or interdentium.

An electric toothbrush according to the present invention is provided with a casing which also serves as a handle, the linear actuator according to the present invention described above which is installed in the casing, and a replacement brush which is removably attached to an end portion of the output member of the linear actuator which projects from the casing to outside.

Since the linear actuator is used in this electric toothbrush, the same functional effect as described above can be obtained. Namely, it is possible to form a magnetic circuit from the magnetic pole of the permanent magnet which does not face the coil to the coil by means of the yoke by tightly fixing the midway portion of the yoke to the magnetic pole of the permanent magnet which does not face the coil and disposing the end portion of the yoke close to the exterior of the coil. As a result, the magnetic leakage of the permanent magnet can be reduced, thereby making it possible to improve a magnetic efficiency of the linear actuator. Further, since the yoke serves as a magnetic shield for the coil and permanent magnet, it is possible to reduce the magnetic leakage from the coil and the permanent magnet to the outside and thereby prevent an adverse effect on another device caused by the magnetic leakage before it occurs. Furthermore, it is possible to have the permanent magnet serve as a weight for increasing the inertial force of the output member since the permanent magnet is fixed to the output member. Therefore, it becomes possible to increase the brushing force by the cleaning head without increasing the number of parts and weight.

ADVANTAGEOUS EFFECTS OF INVENTION

According to the linear actuator of the present invention, it is possible to form a magnetic circuit from the magnetic pole of the permanent magnet which does not face the coil to the coil by means of the yoke by tightly securing the midway portion of the yoke to the magnetic pole of the permanent magnet which does not face the coil and disposing the end portion of the yoke close to the exterior of the coil. As a result, the magnetic leakage of the permanent magnet can be reduced, thereby making it possible to improve the magnetic efficiency of the linear actuator. Further, since the yoke serves as a magnetic shield for the coil and permanent magnet, it is possible to reduce the magnetic leakage from the coil and the permanent magnet to the outside without increasing the number of parts and thereby prevent an adverse effect on another devices caused by the magnetic leakage before it occurs. Furthermore, it is possible to have the permanent magnet serve as a weight for increasing the inertial force of the output member because the permanent magnet is fixed to the output member. Therefore, it becomes possible to increase the inertial force of the output member without increasing the number of parts and weight. As a result of this, in a case where this linear actuator is used as driving means for linearly reciprocating a cleaning head of an electric toothbrush, for example, it is possible to increase a brushing force by the cleaning head without increasing the number of parts and weight.

DESCRIPTION OF EMBODIMENTS

Hereinafter, embodiments of the present invention will be described with reference to the drawings. In this regard, the present embodiments refer to a case where the linear actuator according to the present invention is applied to an electric toothbrush.

First Embodiment

Figure 1:
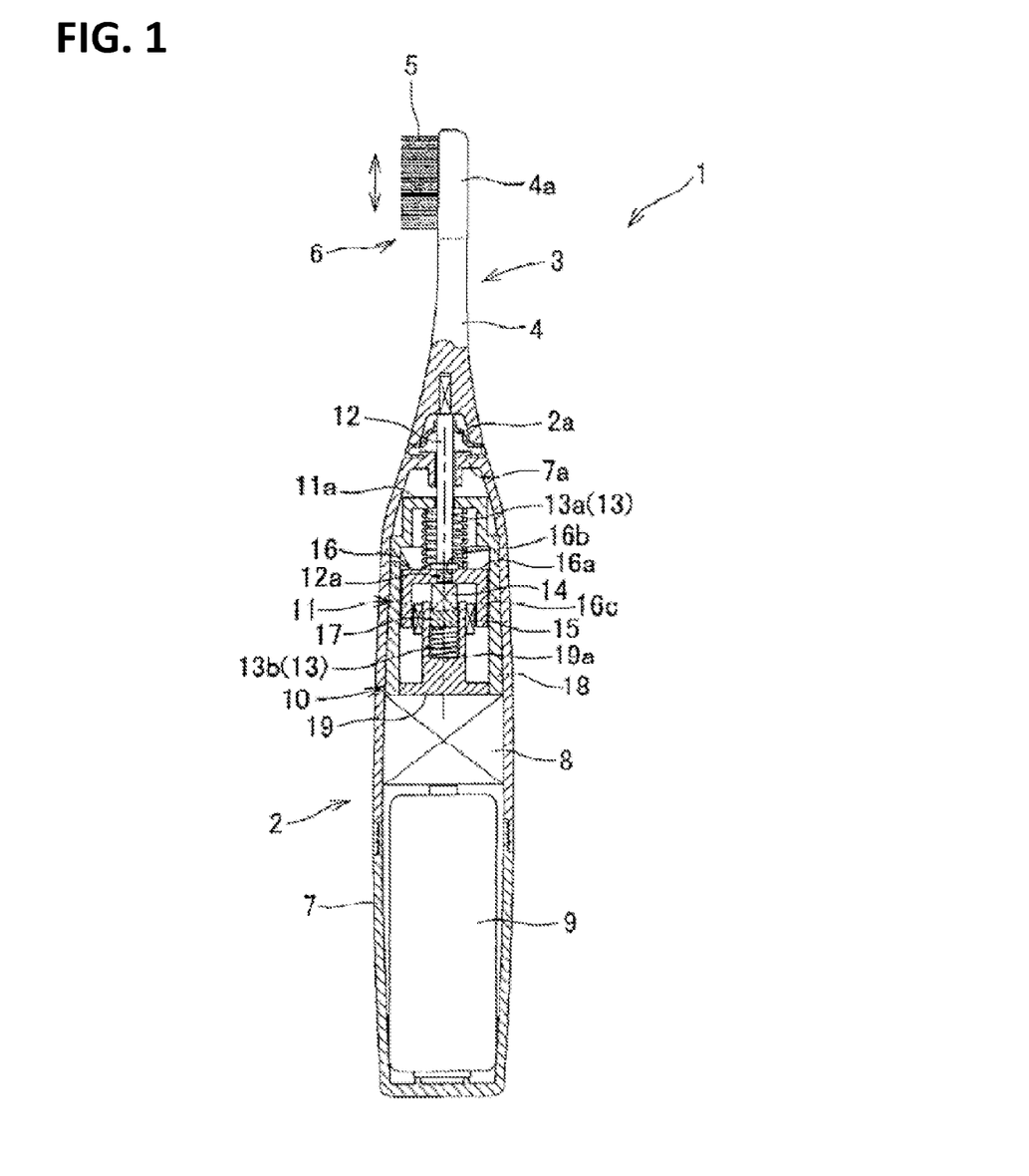
FIG. 1 is a vertical cross-sectional view illustrating an electric toothbrush of the first embodiment.
Figure 2:
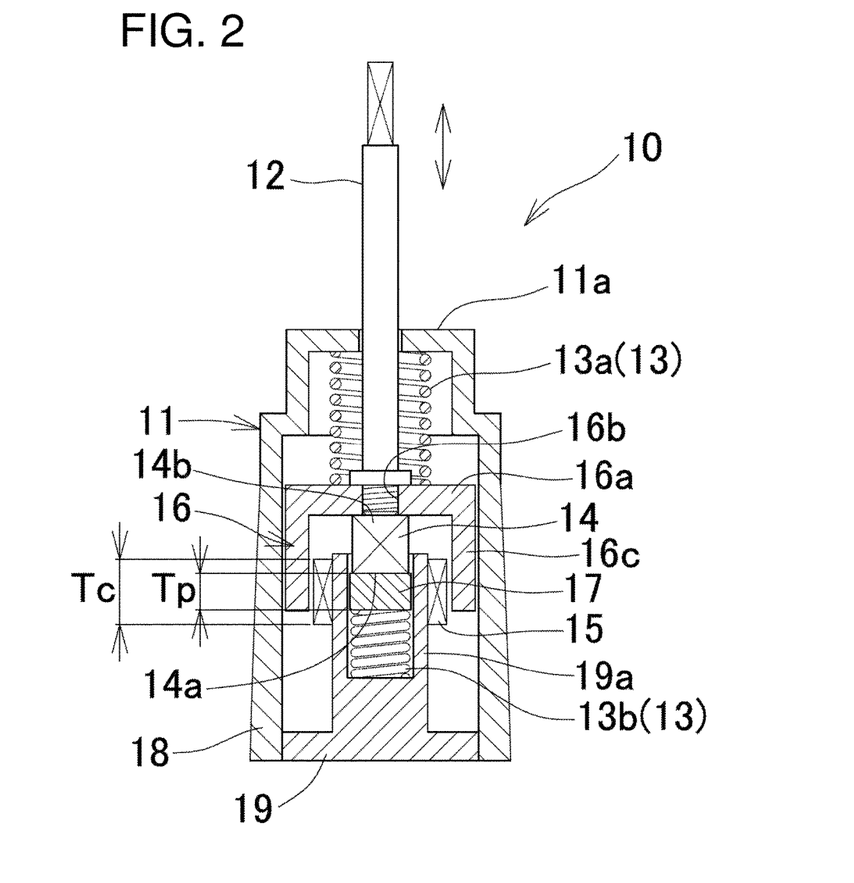
FIG. 2 is a vertical cross-sectional view illustrating a linear actuator body of the first embodiment.

As shown in FIG. 1 and FIG. 2, an electric toothbrush 1 is provided with an electric toothbrush body 2 and a replacement brush 3 which is removably attached to an output shaft 12, which is equivalent to the output member, of the electric toothbrush body 2, wherein the replacement brush 3 is linearly reciprocated together with the output shaft 12 in an axis direction of the output shaft 12 so as to brush teeth.

The replacement brush 3, which has a well-known structure, includes a rod-like and short body member 4 whose end portion has an implant mount 4a and a plurality of bristle bundles 5 formed by bundling a plurality of filaments and is configured to be able to brush teeth with a cleaning head 6 which includes the implant mount 4a and the bristle bundles 5 implanted on the implant mount 4a. It is possible to employ a filament having a well-known configuration such as one whose tip is formed into a sharpened shape or a hemispherical shape, or divided into a plurality of fine fibers. Further, it is also possible to arbitrarily determine the number of filaments which forms the bristle bundles 5 and an arrangement, a shape, the number and the like of bristle bundles 5 which are to be implanted on the implant mount 4a. Furthermore, also with regard to a joint structure of the replacement brush 3 with respect to the output shaft 12, a well-known joint structure in which the replacement brush 3 is fitted into the output shaft 12 until it clicks and does not come off easily can be employed.

The electric toothbrush body 2 includes a casing 7 having a vertically elongated and generally cylindrical shape which also serves as a handle to be held by hand, a linear actuator body 10 which is embedded inside an upper part of the casing 7, a control unit 8 which is placed inside a midway part of the casing 7, and a battery 9 loaded inside a lower part of the casing 7. In this regard, the linear actuator is composed of the linear actuator body 10, the control unit 8, and the battery 9, and the power supply means is composed of the control unit 8 and the battery 9.

A primary battery or a secondary battery can be preferably used as the battery 9. In case of using the primary battery, the casing 7 is configured to be able to change the battery 9. On the other hand, in case of using the secondary battery, the casing 7 is configured such that the battery 9 is mounted inside the casing 7 so that consumers cannot change the battery 9 easily and charged with a wired or wireless manner. A nickel-cadmium battery, a lithium-ion battery, a nickel-hydrogen battery and the like can be utilized as the secondary battery. It is also possible to use an external power source such as alternating current for domestic use instead of the battery 9.

The linear actuator body 10 is provided with a supporting case 11 as the fixing-side member which is embedded inside the upper part of the casing 7, an output shaft 12 which extends upward through a top wall portion 7a of the casing 7 and a top wall portion 11a of the supporting case 11 so as to linearly reciprocate freely, an elastic member 13 which biases the output shaft 12 toward a middle position of the linear reciprocation thereof, a permanent magnet 14 which is fixed to the output shaft 12, a coil 15 which linearly reciprocates the output shaft 12 by having a variable magnetic field act on the permanent magnet 14 and is fixed to the supporting case 11 such that the coil 15 faces a magnetic pole 14a which is one of magnetic poles of the permanent magnet 14, and a yoke 16, which is composed of a magnetic material, has a midway portion tightly secured to the other magnetic pole 14b of the permanent magnet 14, extends to the exterior of the coil 15 along exterior of the permanent magnet 14 with a space from the permanent magnet 14, has an end portion disposed close to the exterior of the coil 15. Further, the linear actuator body 10 is configured such that the coil 15 is fixed to the supporting case 11 and the replacement brush 3 is linearly reciprocated through the output shaft 12 by a moving member which is composed of the permanent magnet 14, the yoke 16, and a pole piece 17 as the magnetic path forming member which will be described later. In this regard, the elastic member 13 may be configured so as to bias the output shaft 12 directly or also indirectly through the permanent magnet 14, the yoke 16, the pole piece 17 and the like as shown in FIG. 1 and FIG. 2, as long as it is provided so as to bias the output shaft 12 toward the middle position of the linear reciprocation.

In this case, a size of the linear actuator body 10 is in the range of 15 to 40 mm and preferably in the range of 25 to 35 mm in outer diameter, and in the range of 30 to 100 mm and preferably in the range of 50 to 70 mm in height of a portion excepting the output shaft 12. Further, a moving distance of the output shaft 12 by its linear reciprocation is in the range of 0.3 to 5 mm and preferably in the range of 0.5 to 1 mm.

The supporting case 11 is composed of a bottomed cylindrical supporting case body 18 whose lower end is opened and a lid member 19 which is fixed to the lower end portion of the supporting case body 18 in order to close the opened lower end portion of the supporting case body 18. A cylindrical tubular portion 19a is integrally formed on a central portion of the lid member 19 so as to extend upward from the lid member 19. The cylindrical coil 15 is provided so as to be fitted onto the outside of an upper portion of the tubular portion 19a by winding a winding around it. In the present invention, since magnetic leakage to the outside is suppressed by the yoke 16 as described later, it is possible to form the supporting case 11 from a lightweight synthetic resin material composed of a nonmagnetic material. Therefore, it is also possible to use the upper portion of the casing 7 of the electric toothbrush 1 as the supporting case body 18 without providing the supporting case body 18.

The output shaft 12 is provided through the top wall portion 7a of the casing 7 and the top wall portion 11a of the supporting case 11 so as to be movable in the up and down direction. An upper end portion of the output shaft 12 is protruded upward from the casing 7 and a lower end portion thereof is placed inside the supporting case 11. A rubber cover 2a is provided between an upper end portion of the casing 7 and a neighbor portion of the upper end portion of the output shaft 12 so as to cover a sliding area between the casing 7 and the output shaft 12, thereby preventing water and the like from entering into the inside of the casing 7 from the sliding portion of the output shaft 12 and the casing 7.

The bottomed cylindrical yoke 16 which is composed of a magnetic material is vertically movably provided inside the supporting case 11 such that an opening thereof faces downward. A screw hole 16b is formed on a central portion of a top wall portion 16a of the yoke 16 and a screw portion 12a to be screwed with the screw hole 16b is formed on a lower end portion of the output shaft 12. The output shaft 12 is integrally connected to the yoke 16 by screwing the screw portion 12a into the screw hole 16b. However, the output shaft 12 can be connected to the yoke 16 using other methods such as welding.

The magnetic pole 14b of the permanent magnet 14 is tightly secured to a lower surface of the generally discoid top wall portion 16a of the yoke 16. A generally cylindrical circumferential wall portion 16c is formed on an outer circumferential portion of the top wall portion 16a of the yoke 16 concentrically with the permanent magnet 14 so as to extend downward to surround an outer surface of the permanent magnet 14 with a space from the permanent magnet 14. A lower end portion of the circumferential wall portion 16c of the yoke 16 is fitted to the exterior of the coil 15 such that a tiny gap is uniformly formed therebetween over a whole circumference thereof. The disc-shaped pole piece 17 is tightly secured to the magnetic pole 14a of the permanent magnet 14 and the pole piece 17 is fitted to the inside of the coil 15 such that a tiny gap is uniformly formed therebetween over a whole circumference thereof. By disposing the coil 15 between the end portion of the circumferential wall portion 16c of the yoke 16 and the pole piece 17 which faces the end portion of the circumferential wall portion 16c in this way, it is possible to form a magnetic circuit with small magnetic leakage. In addition to this, since the permanent magnet 14, the pole piece 17 and the coil 15 are surrounded by the yoke 16 which is composed of a magnetic material, it is possible to prevent magnetic leakage to the outside of the supporting case 11, as a result of which an adverse effect on another device caused by the magnetic leakage can be prevented.

A positional relationship in a height direction between the coil 15, the yoke 16 and the pole piece 17 is to be determined such that a central portion of the coil 15 in a height direction and a central portion of the pole piece 17 in a height direction are located on the relatively same level and further, a lower end portion of the pole piece 17 and the lower end portion of the circumferential wall portion 16c of the yoke 16 are located on the relatively same level, at the middle position of the linear reciprocation. A thickness of the pole piece 17 and a length of the coil 15 in a centerline direction (a length in the up and down direction) may be appropriately set in accordance with the moving distance of the linear reciprocation. For example, the thickness of the pole piece 17 may be set in the range of 3 to 20 mm and preferably in the range of 3 to 10 mm. The length of the coil 15 in the centerline direction (a winding length) Tc may be set so as to satisfy the relationship $Tp/3 \leq Tc \leq 3Tp$ and preferably satisfy the relationship $Tp/2 \leq Tc \leq 2Tp$, where Tp denotes the thickness of the pole piece 17. Further, a diameter of the coil 15 and a diameter of the winding which constitutes the coil 15 may be set in accordance with a brushing force to be required. For example, the diameter of the coil 15 may be set in the range of 6 to 35 mm and preferably in the range of 8 to 25 mm, and further, the diameter of the winding may be set in the range of 0.1 to 2 mm and preferably in the range of 0.2 to 1 mm. In this regard, not only a round wire having a round cross-sectional shape but also a flat wire having a square cross-sectional shape can be used as the winding. Further, the number of turns of the winding constituting the coil 15 may be set in accordance with the winding length of the winding. Specifically, the number of turns of the winding (a wound layer) may be set so as to be 1 to 10 layers and preferably to be 2 to 8 layers. In this way, specifications of the coil 15 such as the diameter of the coil 15, the diameter of the winding, the winding length and the like can be determined in accordance with a distance (a magnetic gap length) between the pole piece 17 and the yoke 16 and the thickness of the pole piece 17.

Figure 3:
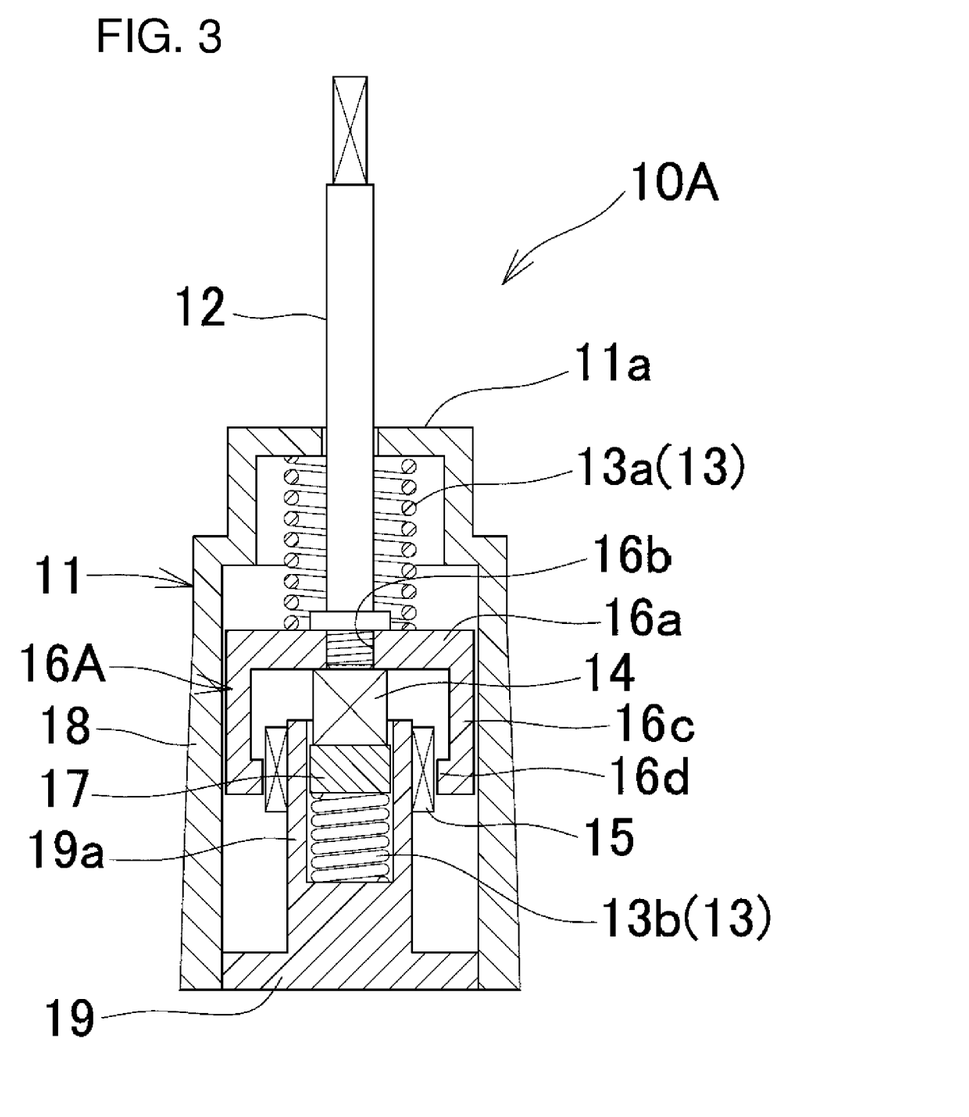
FIG. 3 is a vertical cross-sectional view illustrating a linear actuator body of another configuration.

Further, it is also a preferred embodiment that a yoke 16A which includes a bent portion 16d formed by bending the lower end portion of the circumferential wall portion 16c inwardly is used instead of the yoke 16, wherein the yoke 16A is disposed such that an end surface of the bent portion 16d faces the coil 15, as a linear actuator body 10A shown in FIG. 3. In this case, although a manufacturing cost of the yoke 16A becomes high, this embodiment is preferable because it is possible to focus a magnetic flux from the lower end portion of the yoke 16A toward the coil 15 and thereby further improve a magnetic efficiency. Furthermore, although the yoke 16A can be constructed of a single member, in order to increase formability at the bent portion 16a, a ring-shaped or cylindrical plate having a hollow portion whose diameter is smaller than the opening portion of the yoke 16 may also be fixed to the lower end surface of the yoke 16 or fitted and fixed onto the inside of the lower end portion of the yoke 16 so as to form the bent portion 16a, thereby making it possible to obtain the same structure as the yoke 16A.

As for the elastic member 13, a first spring member 13a which downwardly biases the yoke 16 is fitted onto the exterior of the output shaft 12 between the top wall portion 11a of the supporting case 11 and the top wall portion 16a of the yoke 16. On the other hand, a second spring member 13b which upwardly biases the pole piece 17 is provided inside the tubular portion 19a of the lid member 19. The output shaft 12 is biased to the middle position (a neutral position) of the linear reciprocation thereof together with the moving member composed of the permanent magnet 14, the yoke 16, and the pole piece 17 by both of the spring members 13a and 13b and elastically held in the middle position. Further, the yoke 16 is disposed such that the lower end portion of the yoke 16 is located on the relatively same level as the lower end portion of the coil 15 and an inner circumferential surface of the lower end portion of the yoke 16 faces an outer surface of the coil 15 with a tiny gap therebetween at the middle position of the linear reciprocation. The pole piece 17 is disposed so as to face a generally central portion of an inner circumferential surface of the coil 15 in a height direction with a tiny space therebetween at the middle position of the linear reciprocation. However, each of the first spring member 13a and the second spring member 13b may be disposed in a position other than the position shown in FIGS. 1 and 2 as long as they can elastically bias the output shaft 12 to the middle position of the linear reciprocation together with the moving member composed of the yoke 16, the permanent magnet 14, and the pole piece 17. Further, it is not always necessary to use a coil spring as the elastic member 13 and it is also possible to utilize an elastic member such as a plate spring, a disc spring, a synthetic rubber and the like.

The control unit 8 has a well-known structure in which a direct current is converted into an alternating current through an inverter circuit and the like. Namely, a generated alternating current is applied to the coil 15 so as to generate an alternating magnetic field on the coil 15. In this regard, the magnetic field generated on the coil 15 is not necessarily an alternating magnetic field. For example, it is also possible to apply a pulsating current to the coil 15 so as to generate a varying magnetic field on the coil 15. When designing the electric toothbrush 1, a frequency of the cleaning head 6 is firstly set to be a value suitable for brushing, for example. Then, a natural frequency of the moving member composed of the permanent magnet 14, the yoke 16, the pole piece 17, the output shaft 12, and the replacement brush 3 is set so as to be a desired value based on the frequency of the cleaning head 6, and further, a frequency of the alternating current is set so as to resonate with the natural frequency of the moving part.

In the electric toothbrush 1, since the coil 15 is fixed to the casing 7 of the electric toothbrush 1 through the supporting case 11, when the alternating magnetic field is formed on the coil 15 by an electric current from the control unit 8, the replacement brush 3 is linearly reciprocated with constant strokes through the output shaft 12 in the axis direction of the output shaft 12 together with the moving member composed of the permanent magnet 14, the yoke 16, and the pole piece 17. Accordingly, the cleaning head 6 brushes teeth by utilizing the linear reciprocation of the replacement brush 3.

Further, in the electric toothbrush 1, the pole piece 17 is attached to the magnetic pole 14a which is one of the magnetic poles of the permanent magnet 14, the pole piece 17 is disposed inside the coil 15 with a tiny space therebetween, the midway portion of the yoke 16 is tightly secured to the other magnetic pole 14b of the permanent magnet 14, and the end portion of the yoke 16 is disposed close to the exterior of the coil 15. This makes it possible to form a magnetic circuit with small magnetic leakage by the permanent magnet 14, the pole piece 17, the yoke 16, and the coil 15. Accordingly, it becomes possible to reduce the magnetic leakage of the permanent magnet 14 and thereby improve a magnetic efficiency of the linear actuator body 10. As a result, the brushing force by the cleaning head 6 can be increased. Further, since the yoke 16 serves as a magnetic shield for the coil 15 and the permanent magnet 14, the magnetic leakage to the outside of the casing 7 can be reduced without increasing the number of parts. Accordingly, it is possible to prevent an adverse effect on another device caused by the magnetic leakage before it occurs. Furthermore, since the permanent magnet 14 is fixed to the output shaft 12, it is possible to have the permanent magnet 14 serve as a weight for increasing the inertial force of the output shaft 12. As a result, it is possible to increase the inertial force of the output shaft 12 without increasing the number of parts or weight, thereby the brushing force by the cleaning head 6 can be increased.

Second Embodiment

Next, a linear actuator body according to the second embodiment which can be used in an electric toothbrush will be described. In this regard, only a structure of the linear actuator body will be described because structures of other parts than the linear actuator body can be made to be the same as the first embodiment described above.

Figure 4:
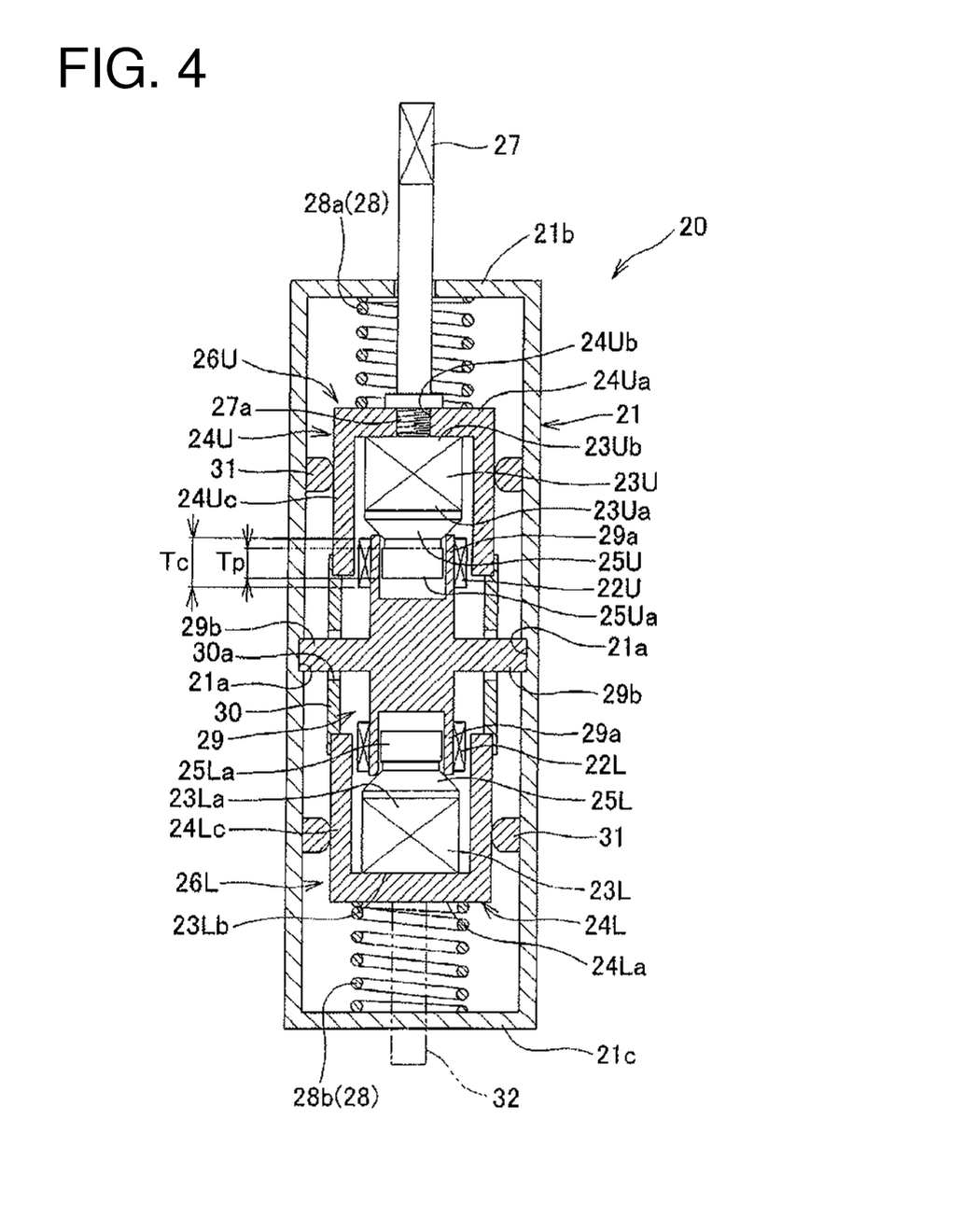
FIG. 4 is a vertical cross-sectional view illustrating a linear actuator body of the second embodiment.

As shown in FIG. 4, a linear actuator body 20 of the second embodiment is provided with a cylindrical supporting case 21 in which both upper and lower end portions thereof are closed; two magnetic units 26U and 26L disposed in series inside the supporting case 21 such that they face each other so as to be vertically symmetric wherein the magnetic unit 26U is composed of a coil 22U, a permanent magnet 23U, a yoke 24U, and a pole piece 25U and the magnetic unit 26L is composed of a coil 22L, a permanent magnet 23L, a yoke 24L, and a pole piece 25L; an output shaft 27 which extends upward through a top wall portion 21b of the supporting case 21 and a lower end portion of which is secured to a top wall portion 24Ua of the upper yoke 24U; elastic members 28 which bias the output shaft 27 toward an middle position of linear reciprocation of the output shaft 27; a supporting member 29 which immovably supports the coil 22U and the coil 22L in a midway portion of the supporting case 21 in a height direction; a connecting member 30 which integrally connects an upper moving member composed of the permanent magnet 23U, the yoke 24U, and the pole piece 25U with a lower moving member composed of the permanent magnet 23L, the yoke 24L, and the pole piece 25L; and guide members 31 which guide the two moving members connected by the connecting member 30 such that the moving members can linearly reciprocate freely in the up and down direction with respect to the supporting case 21.

The supporting case 21 is composed of a cylindrical member in which both upper and lower end portions are closed. Further, the supporting case 21 are divided into two divided bodies by a dividing surface including a centerline thereof and configured to be able to embed the two magnetic units 26U and 26L inside thereof by combining the two divided bodies. On a midway portion of an inner surface of the supporting case 12 in a height direction, there are formed four fitting concave portions 21a with a certain space with each other in a circumferential direction. Further, a supporting member 29 composed of four arm portions 29b which are arranged so as to form a cross shape is placed in the midway portion of the supporting case 21 in a height direction. The supporting member 29 is immovably and fixedly supported in a generally central portion of the supporting case 21 in a height direction such that end portions of the four arm portions 29b are respectively fitted onto the four fitting concave portions 21a. In this regard, the number of the fitting concave portions 21a may be set to be a plural number other than four, and further, the number of the arm portions 29b may be set to be a plural number corresponding to the number of the fitting concave portions 21a.

The supporting member 29 is a member corresponding to the lid member 19 of the first embodiment described above. Upper and lower cylindrical tubular portions 29a are formed on a central portion of the supporting member 29 so as to protrude upwardly and downwardly, respectively. The coils 22U and 22L each of which is composed of a winding wound in a cylindrical configuration are fitted and fixed onto the exterior of an upper end portion of the upper tubular portion 29a and the exterior of a lower end portion of the lower tubular portion 29a, respectively.

Each of the upper yoke 24U and the lower yoke 24L is composed of a bottomed cylindrical magnetic material as with the first embodiment. The yoke 24U in the upper magnetic unit 26U is secured to a lower end portion of the output shaft 27 inside the upper divided body of the supporting case 21 above the supporting member 29 with its opening facing downward. The yoke 24L in the lower magnetic unit 26L is arranged inside the lower divided body of the supporting case 21 below the supporting member 29 with its opening facing upward and in an opposing relationship with respect to the yoke 24L across the supporting member 29.

A screw hole 24Ub is formed on a central portion of an top wall portion 24Ua of the yoke 24U. Further, a screw portion 27a to be screwed with the screw hole 24Ub is formed on the lower end portion of the output shaft 27. The output shaft 27 is integrally connected to the yoke 24U by screwing the screw portion 27a with the screw hole 24Ub. However, it is also possible to connect the output shaft 27 with the yoke 24U by another method such as welding.

A cylindrical connecting member 30 is provided between the upper yoke 24U and the lower yoke 24L such that the upper yoke 24U and the lower yoke 24L are connected so as to linearly reciprocate integrally in an axis direction of the output shaft 27 through the connecting member 30. There are formed four vertically-elongated slots 30a on a midway portion of the connecting member 30 in a height direction with a certain space between each other in a circumferential direction thereof. The connecting member 30 is divided into two semicylindrical divided bodies by a dividing surface which includes a centerline of the connecting member 30 and divides a pair of opposing slots 30a. The four arm portions 29b of the supporting member 29 are respectively inserted into the four slots 30a at midway portions thereof so that the supporting member 29 is embedded inside the connecting member 30 so as to be moveable in the axis direction of the output shaft 27 within a linear reciprocation range of the output shaft 27. In this regard, the connecting member 30 of any configuration may be used as long as it can integrally connect the upper yoke 24U with the lower yoke 24L.

The ring-shaped guide members 31 are disposed inside an upper part and a lower part of the supporting case 21, respectively. A circumferential wall portion 24Uc of the upper yoke 24U and a circumferential wall portion 24Lc of the lower yoke 24L are movably guided in the up and down direction by the guide members 31, which means that the upper moving member composed of the permanent magnet 23U, the yoke 24U, and the pole piece 25U, the lower moving member composed of the permanent magnet 23L, the yoke 24L, and the pole piece 25L, the connecting member 30 which connects the upper and lower moving members, and the output shaft 27 are integrally guided so as to linearly reciprocate freely in the axis direction of the output shaft 27 inside the supporting case 21. In this regard, the guide member 31 of any configuration may be used as long as it can guide the upper and lower moving members so as to linearly reciprocate freely in the axis direction of the output shaft 27 inside the supporting case 21. Further, it is also a preferred embodiment that, instead of the guide members 31, a guide shaft 32 extending downward through a bottom wall portion 21c of the supporting case 21 is secured to a central portion of a bottom wall portion 24La of the lower yoke 24L so as to be concentric with the output shaft 27 as indicated by a virtual line in FIG. 4, and the upper and lower moving members are movably guided in the up and down direction together with the connecting member 30 by the output shaft 27 and the guide shaft 32.

As for the elastic member 28, a first spring member 28a which downwardly biases the upper and lower moving members connected with each other by the connecting member 30 is fitted onto the exterior of the output shaft 27 between the top wall portion 21b of the supporting case 21 and the top wall portion 24Ua of the upper yoke 24U. On the other hand, a second spring member 28b which upwardly biases the upper and lower moving members connected with each other by the connecting member 30 is provided between the bottom wall portion 21c of the supporting case 21 and the bottom wall portion 24La of the lower yoke 24L. The output shaft 27 is biased to the middle position (a neutral position) of the linear reciprocation thereof by the first spraying member 28a and the second spraying member 28b, and elastically held in the middle position. In this regard, the elastic member 28 may be configured so as to bias the output shaft 27 directly or also indirectly through the yokes 24U and 24L, the permanent magnets 23U and 23L, the pole pieces 25U and 25L, and the like as shown in FIG. 4 as long as it is provided so as to bias the output shaft 27 toward the middle position of the linear reciprocation thereof.

A lower end portion of the circumferential wall portion 24Uc of the upper yoke 24U is arranged around the upper coil 22U so as to face an outer circumferential surface of the upper coil 22U with a uniform tiny gap therebetween over a whole circumference of the coil 22U. The upper permanent magnet 23U has a magnetic pole 23Ub which is tightly secured to a central portion of a lower surface of the top wall portion 24Ua of the upper yoke 24U and the magnetic pole 23Ua located on the bottom end surface thereof to which the pole piece 25U is tightly secured. A cylindrical portion 25Ua located on a lower part of the pole piece 25U is disposed inside the upper coil 22U so as to face an inner circumferential surface of the coil 22U with a uniform tiny gap therebetween over a whole circumference of the coil 22U.

A positional relationship in a height direction between the coil 22U, the yoke 24U, and the pole piece 25U is to be determined such that a central portion of the coil 22 in a height direction and a central portion of the cylindrical portion 25Ua of the pole piece 25U in a height direction are located on the relatively same level and further, a lower end portion of the pole piece 25U and a lower end portion of the circumferential wall portion 24Uc of the yoke 24U are located on the relatively same level, at the middle position of the linear reciprocation. A thickness of the cylindrical portion 25Ua of the pole piece 25U and a length of the coil 22U in a centerline direction (a length in the up and down direction) may be appropriately set in accordance with a moving distance of the linear reciprocation. For example, the thickness of the cylindrical portion 25Ua may be set in the range of 3 to 20 mm and preferably in the range of 3 to 10 mm. The length of the coil 22U in the centerline direction (a winding length) Tc may be set so as to satisfy the relationship $Tp/3 \leq Tc \leq 3Tp$ and preferably satisfy the relationship $Tp/2 \leq Tc \leq 2Tp$, where Tp denotes the thickness of the cylindrical portion 25Ua. Further, a diameter of the coil 22U and a diameter of the winding which constitutes the coil 22U may be set in accordance with a brushing force to be required. For example, the diameter of the coil 22U may be set in the range of 6 to 35 mm and preferably in the range of 8 to 25 mm, and further, the diameter of the winding may be set in the range of 0.1 to 2 mm and preferably in the range of 0.2 to 1 mm. In this regard, not only a round wire having a round cross-sectional shape but also a flat wire having a square cross-sectional shape can be used as the winding. Further, the number of turns of the winding which constitutes the coil 22U may be set in accordance with the winding length of the winding. Specifically, the number of turns of the winding (a wound layer) may be set so as to be 1 to 10 layers and preferably to be 2 to 8 layers. In this way, specifications of the coil 22U such as the diameter of the coil 22U, the diameter of the winding, the winding length and the like can be determined in accordance with a distance (a magnetic gap length) between the cylindrical portion 25Ua of the pole piece 25U and the yoke 24U and the thickness of the cylindrical portion 25Ua. In this regard, a detailed description with regard to the coil 22L, the yoke 24L, and the pole piece 25L will be omitted because each of the coil 22L, the yoke 24L, and the pole piece 25L is arranged so as to be an inversion of the coil 22U, the yoke 24U, and the pole piece 25U, respectively.

By disposing the coil 22U between the end portion of the circumferential wall portion 24Uc of the yoke 24U and the facing pole piece 25U so as to be close to each other with a tiny gap therebetween and also the coil 22L between the end portion of the circumferential wall portion 24Lc of the yoke 24L and the facing pole piece 25L so as to be close to each other with a tiny gap therebetween, it is possible to form a magnetic circuit with small magnetic leakage. In addition to this, since the permanent magnet 23U, the pole piece 25U, and the coil 22U are surrounded by the yoke 24U which is composed of a magnetic material and the permanent magnet 23L, the pole piece 25L, and the coil 22L are surrounded by the yoke 24L which is composed of a magnetic material, it is possible to prevent magnetic leakage to the outside of the supporting case 21, as a result of which an adverse effect on another device caused by the magnetic leakage can be prevented.

The linear actuator body 20 is to be used in such a state that it is embedded inside the upper portion of the casing 7 of the electric toothbrush 1 as with the linear actuator body 10 of the first embodiment described above. Further, since the coils 22U and 22L are fixed to the casing 7 of the electric toothbrush 1 through the supporting member 29 and the supporting case 21 in such an embedded state, when an alternating magnetic field is formed on each of the coils 22U and 22L by an electric current from the control unit 8, the upper moving member composed of the permanent magnet 23U, the yoke 24U, and the pole piece 25U and the lower moving member composed of the permanent magnet 23L, the yoke 24L, and the pole piece 25L are linearly reciprocated with constant strokes in the axis direction of the output shaft 27 integrally through the connecting member 30. Accordingly, the replacement brush 3 is linearly reciprocated with constant strokes in the axis direction of the output shaft 27 through the output shaft 27 and the cleaning head 6 brushes teeth by utilizing the linear reciprocation of the replacement brush 3.

In the linear actuator body 20, variable magnetic fields are synchronously formed with respect to each of the two coils 22U and 22L by the control unit 8, thus, it is possible to have a driving force twice as large as that of the electric toothbrush 1 of the above described first embodiment act on the output shaft 27 to thereby linearly reciprocate the cleaning head 6. Further, as for the upper magnetic unit 26U in the linear actuator body 20, the pole piece 25U is attached to the magnetic pole 23Ua of the permanent magnet 23U and disposed inside the coil 22U with a tiny gap from the coil 22U. In addition, the midway portion of the yoke 24U is tightly secured to the magnetic pole 23Ub of the permanent magnet 23U and the end portion of the yoke 24U is disposed close to the exterior of the coil 22U. Accordingly, it is possible to form a magnetic circuit with small magnetic leakage by the permanent magnet 23U, the pole piece 25U, the yoke 24U, and the coil 22U. Furthermore, as for the lower magnetic unit 26L, it is also possible to form a magnetic circuit with small magnetic leakage by the permanent magnet 23L, the pole piece 25L, the yoke 24L, and the coil 22L in the same manner as the upper magnetic unit 26U. Therefore, it becomes possible to reduce the magnetic leakage of the permanent magnets 23U and 23L and thereby improve a magnetic efficiency of the linear actuator body 20. As a result, the brushing force by the cleaning head 6 can be increased. Further, since the yoke 24U serves as a magnetic shield for the coil 22U and the permanent magnet 23U and the yoke 24L serves as a magnetic shield for the coil 22L and the permanent magnet 23L, the magnetic leakage to the outside of the supporting case 21 can be reduced without increasing the number of parts. Accordingly, it is possible to prevent an adverse effect on another device caused by the magnetic leakage can be prevented before it occurs. Furthermore, since the permanent magnets 23U and 23L, the yokes 24U and 24L, and the pole pieces 25U and 25L are linearly reciprocated together with the output shaft 27, it is possible to have these members serve as a weight for increasing an inertial force of the output shaft 27. As a result, the inertial force of the output shaft 27 can be increased without increasing the number of parts or weight, thereby making it possible to increase the brushing force by the cleaning head 6.

Next, another embodiment in which the structure of the linear actuator body 20 of the above described second embodiment is partially modified will be described. In this regard, the same reference signs as in the linear actuator body 20 of the above described second embodiment are applied to the same members as in the linear actuator body 20 of the second embodiment and detailed descriptions for these members will be omitted.

(1) It is also a preferred embodiment that the end portion of the circumferential wall portion 24Uc of the yoke 24U and the end portion of the circumferential wall portion 24Lc of the yoke 24L are inwardly bent so as to face the coil 22U and the coil 22L, respectively, as with the linear actuator body 10A shown in FIG. 3. In this case, although a manufacturing cost of the yokes 24U and 24L becomes high, it is possible to focus a magnetic flux from each of the lower end portions of the yokes 24U and 24L toward the coils 22U and 22L, respectively, and thereby further improve a magnetic efficiency.

Figure 5:
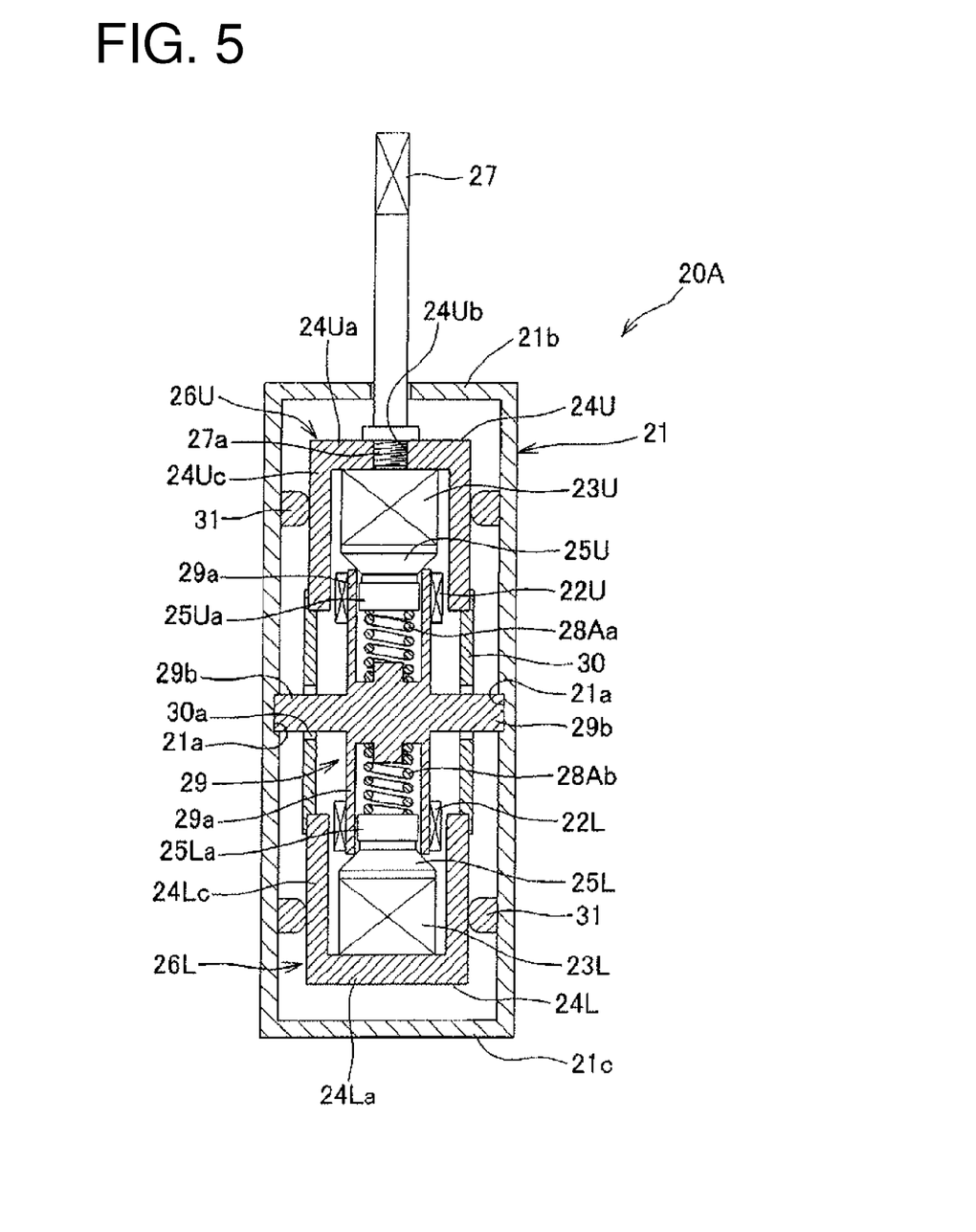
FIG. 5 is a vertical cross-sectional view illustrating a linear actuator body of another configuration.

(2) Each of the first spring member 28a and the second spring member 28b may be provided in a position other than the position shown in FIG. 4 as long as they can elastically bias the upper and lower moving members to the middle position of the linear reciprocation. For example, as a liner actuator body 20A shown in FIG. 5, a first spring member 28Aa may be disposed between the pole piece 25U and a back end surface of the upper tubular portion 29a inside the upper tubular portion 29a, and further, a second spring member 28Ab may be disposed between the pole piece 25L and a back end surface of the lower tubular portion 29a inside the lower tubular portion 29a.

Figure 6:
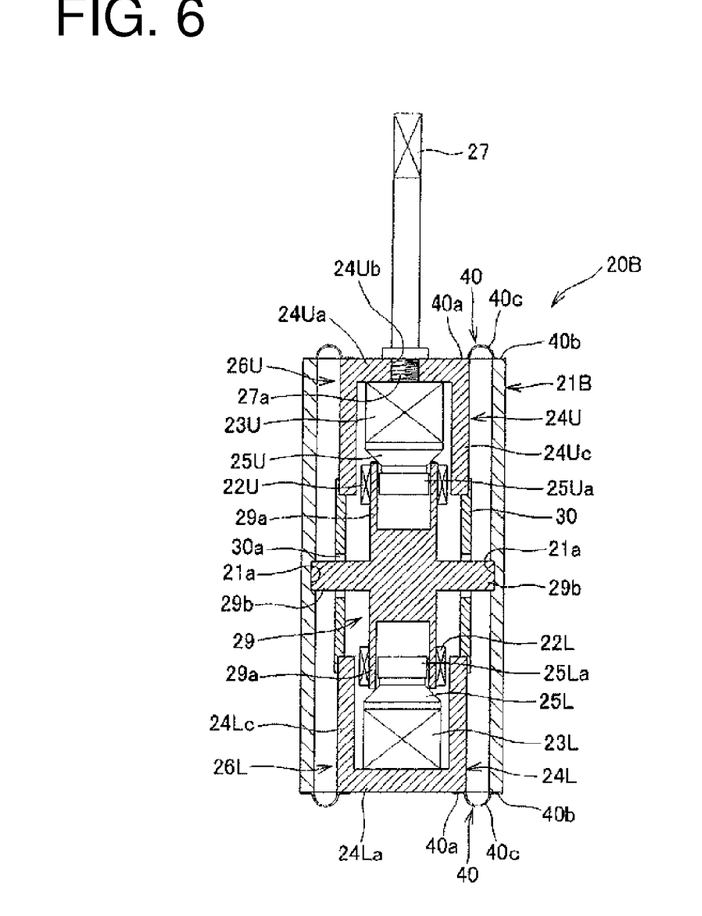
FIG. 6 is a vertical cross-sectional view illustrating a linear actuator body of another configuration.
Figure 7:
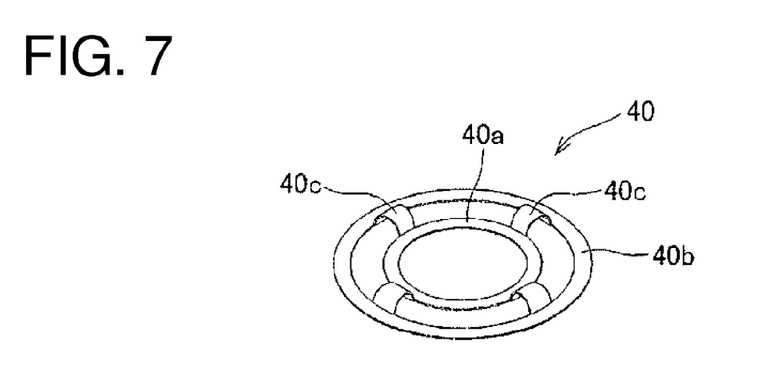
FIG. 7 is a perspective view illustrating an elastic member of the linear actuator body shown in FIG. 6.

(3) It is not always necessary to use a coil spring as the elastic member 28 and it is also possible to utilize an elastic member such as a plate spring, a disc spring, a synthetic rubber and the like. For example, as an linear actuator body 20B shown in FIG. 6 and FIG. 7, it is also a preferred embodiment that the linear actuator body 20B is provided with a cylindrical supporting case 21B, instead of the supporting case 21, both top and bottom surfaces of which are opened; and a pair of upper and lower generally plate-like circular spring members 40, instead of both of the spring members 28a and 28b, which connect an upper end portion of the supporting case 21B with the yoke 24U as well as a lower end portion of the supporting member 21B with the yoke 24L, and each of which has a circular inner circumferential portion 40a and a circular outer circumferential portion 40b which are concentrically arranged and a plurality of arm portions 40c each of which has a circular arc-like cross-sectional shape and end portions connected to the inner circumferential portion 40a and the outer circumferential portion 40b; respectively so as to connect the inner circumferential portion 40a with the outer circumferential portion 40b, wherein the inner circumferential portions 40a of the upper and lower spring members 40 are respectively fixed to the yoke 24U and the yoke 24L while the outer circumferential portions 40b of the upper and lower spring members 40 are respectively fixed to the upper end portion and the lower end portion of the supporting case 21B so as to connect the yokes 24U and 24L with the supporting case 21B by the pair of upper and lower spring members 40. In this linear actuator body 20B, the upper and lower moving members are elastically held in the middle position of the linear reciprocation by the spring members 40. Further, this embodiment is preferable because moving resistance of the moving members at the time of the linear reciprocation can be reduced by omitting the guide member 31. In this regard, an arm portion 40c having a wavelike cross-sectional shape may also be used. Further, it is also possible to provide a continuous circular connecting portion having a circular arc-like cross-sectional shape or a wavelike cross-sectional shape to connect the inner circumferential portion 40a with the outer circumferential portion 40b instead of the arm portion 40c.

Figure 8:
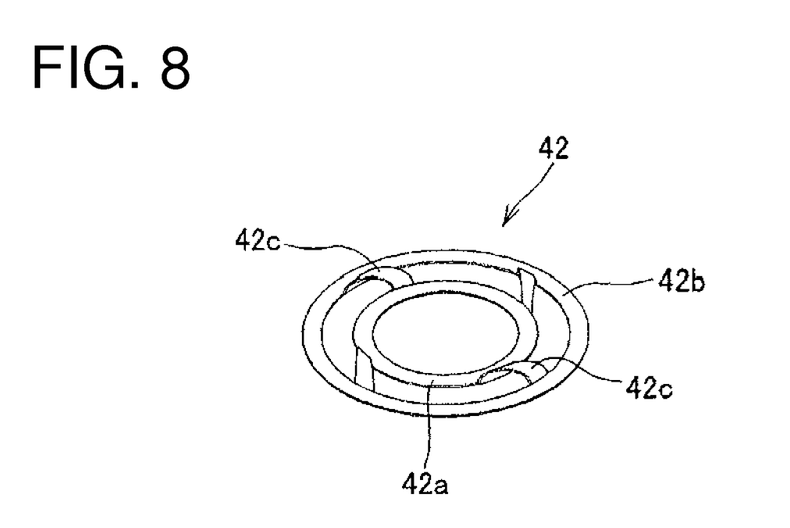
FIG. 8 is a perspective view illustrating an elastic member of another configuration.

Furthermore, as shown in FIG. 8, it is also a preferred embodiment that a pair of upper and lower generally plate-like circular spring members 42 are used instead of the spring members 40, each of the spring members 42 includes a circular inner circumferential portion 42a and a circular outer circumferential portion 42b which are concentrically arranged and a plurality of arm portions 42c which connect the inner circumferential portion 42a with the outer circumferential portion 42b; and both end portions of the arm portion 42c are respectively connected to the inner circumferential portion 42a and the outer circumferential portion 42b such that one end portion of the arm portion 42c is displaced a certain degree of angle from the other end portion with respect to a circumferential direction and the displacement is made for all arm portions 42c with the same angle and the same direction; the inner circumferential portions 42a of the upper and lower spring members 42 are respectively fixed to the yoke 24U and the yoke 24L while the outer circumferential portions 42b are respectively fixed to the upper end portion and the lower end portion of the supporting case 21B so as to connect the yokes 24U and 24L with the supporting case 21B by the pair of upper and lower spring member 42. In this case, the upper and lower moving members are elastically held in the middle position of the linear reciprocation by the spring member 42. In addition, when the upper and lower moving members are linearly reciprocated, the output shaft 27 is inversionally reciprocated around the output shaft 27 together with the moving members due to the deformation of the arm portions 42c of the spring member 42. As a result of this, it is possible to brush teeth efficiently by the linear reciprocation of the cleaning head 6 in the axis direction of the output shaft 27 and the inversional reciprocation of the cleaning head 6 around the output shaft 27.

Figure 9:
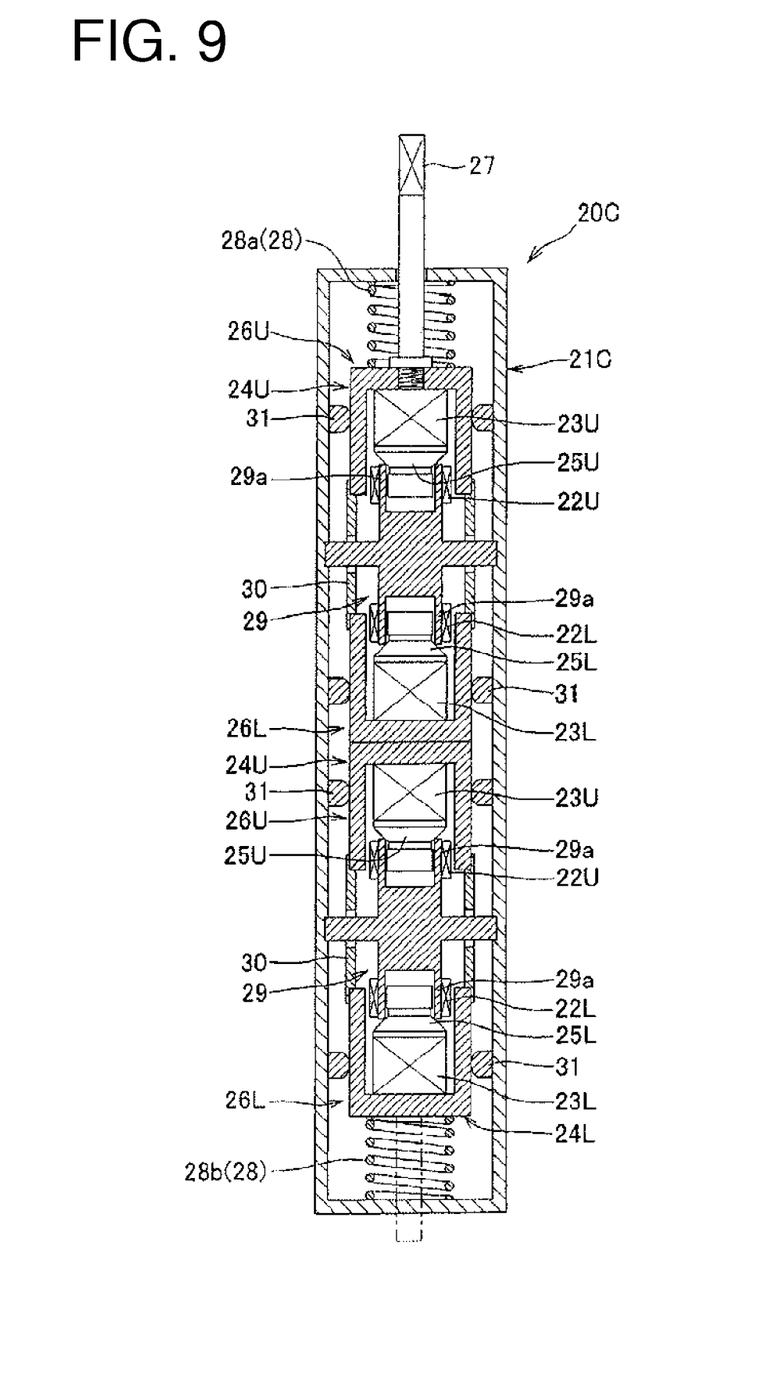
FIG. 9 is a vertical cross-sectional view illustrating a linear actuator body of another configuration.

Although the embodiments in which the output shaft 12 is driven by one magnetic unit and the output shaft 27 is driven by the two magnetic units 26U and 26L connected in series have been described, an output shaft may also be driven by equal to or more than three magnetic units connected in series or by a plurality of magnetic units connected in parallel. Further, it is also possible to connect a plurality of serially-connected magnetic units in parallel. In case of connecting equal to or more than three magnetic units in series, two pairs of the magnetic units 26U and 26L having the same structure as that of the linear actuator body 20 are connected in series one above the other, the connected magnetic units are then installed inside a vertically-elongated supporting case 21C, and moving members of these four magnetic units 26U, 26L are elastically held by the first spring member 28a and the second spring member 28b as a linear actuator body 20C shown in FIG. 9, for example.

Further, although the replacement brush 3 is linearly reciprocated in the axis direction of the output shaft 12 in the present embodiment, it is also possible to have a brushing portion composed of a plurality of the bristle bundles 5 move in another direction by installing a moving direction changing mechanism for changing a moving direction in the replacement brush 3. Specifically, it is possible to linearly reciprocate the brushing portion in a front-back direction or right-left direction perpendicular to the output shaft 12 and the like, inversionally reciprocate the brushing portion around a direction passing through a central portion of the brushing portion and perpendicular to the output shaft 12, and inversionally and reciprocatingly swing the brushing portion around a midway portion of the body member 4 of the replacement brush 3 in a front-back direction or right-left direction and the like. Further, it is also possible to linearly reciprocate only the bristle bundles 5 of the brushing portion in a direction perpendicular to the output shaft 12 with respect to the implant mount 4a. Furthermore, although the linear actuator body according to the present invention is applied to the driving portion of the electric toothbrush 1, it is also possible to attach a gum massager instead of the replacement brush 3 or apply the linear actuator according to the present invention as driving means for various devices provided with an actuating portion which linearly reciprocates such as an electric shaver and an electric pump.

REFERENCE SIGNS LIST 1 electric toothbrush
2 electric toothbrush body
2a rubber cover
3 replacement brush
4 body member
4a implant mount
5 bristle bundle
6 cleaning head
7 casing
7a top wall portion
8 control unit
9 battery
10 linear actuator body
11 supporting case
11a top wall portion
12 output shaft
12a screw portion
13 elastic member
13a spring member
13b spring member
14 permanent magnet
14a magnetic pole
14b magnetic pole
15 coil
16 yoke
16a top wall portion
16b screw hole
16c circumferential wall portion
17 pole piece
18 supporting case body
19 lid member
19a tubular portion
10A linear actuator body
16A yoke
16d bent portion
20 linear actuator body
21 supporting case
21a fitting concave portion
21b top wall portion
21c bottom wall portion
22U coil
23U permanent magnet
23Ua magnetic pole
23Ub magnetic pole
24U yoke
24Ua top wall portion
24Ub screw hole
24Uc circumferential wall portion
25U pole piece
25Ua cylindrical portion
26U magnetic unit
22L coil
23L permanent magnet
23La magnetic pole
23Lb magnetic pole
24L yoke
24La bottom wall portion
24Lc circumferential wall portion
25L pole piece
25La cylindrical portion
26L magnetic unit
27 output shaft
27a spring portion
28 elastic member
28a first spring member
28b second spring member
29 supporting member
29a tubular portion
29b arm portion
30 connecting member
30a slot
31 guide member
32 guide shaft
20A linear actuator body
28Aa spring member
28Ab spring member
20B linear actuator body
21B supporting case
40 spring member
40a inner circumferential portion
40b outer circumferential portion
40c arm portions
42 spring member
42a inner circumferential portion
42b outer circumferential portion
42c arm portions
20C linear actuator body
21C supporting case

What is claimed is:

1. A linear actuator comprising:
a supporting case,
two magnetic units disposed in series inside the supporting case such that the magnetic units face each other so as to be vertically symmetric wherein each of the two magnetic units is composed of a coil, a permanent magnet, a yoke, and a pole piece,
an output shaft that extends upward through the supporting case and a lower end portion of the output shaft is secured to a top wall portion of the yoke that is located at an upper position,
elastic members that bias the output shaft toward an middle position of linear reciprocation of the output shaft,
a supporting member that immovably supports two coils in a midway portion of the supporting case in a height direction,
a connecting member that integrally connects an upper moving member composed of the permanent magnet, the yoke, and the pole piece in one of the two magnetic units with a lower moving member composed of the permanent magnet, the yoke, and the pole piece in the other of the two magnetic units, and
a power supply for forming variable magnetic fields in the coils, wherein
the two moving members connected by the connecting member are provided so as to linearly reciprocate freely in an up and down direction against the supporting case, each of the respective yokes of the upper moving member and the lower moving member is composed of a bottomed cylindrical magnetic material, an opening of the yoke of the upper moving member faces downward, an opening of the yoke of the lower moving member faces upward, and both yokes are arranged in an opposing relationship with respect to each other across the supporting member, and one magnetic pole of the permanent magnet is secured to the pole piece, another magnetic pole of the permanent magnet is secured to an inner bottom portion of the yoke, the coil is disposed between the end portion of the circumferential wall portion of the yoke and the facing pole piece with a gap, thereby to form a magnetic circuit by the permanent magnet, the pole piece, the yoke, and the coil in the upper and lower magnetic units.

2. The linear actuator according to claim 1,
wherein a pair of upper and lower generally plate-like circular spring members, which connect an upper end portion of the supporting case with the upper yoke as well as a lower end portion of the supporting member with the lower yoke, and each of which has a circular inner circumferential portion and a circular outer circumferential portion which are concentrically arranged and a plurality of arm portions each of which has a circular arc-like cross-sectional shape so as to connect the inner circumferential portion with the outer circumferential portion is used as the elastic member.

3. An electric toothbrush comprising:
a casing serving as a handle;
the linear actuator according to claim 1 and disposed in the casing; and
a replacement brush removably attached to an end portion of the output member of the linear actuator, the end portion projecting from the casing to outside.

4. An electric toothbrush comprising:
a casing serving as a handle;
the linear actuator according to claim 2 and disposed in the casing; and
a replacement brush removably attached to an end portion of the output member of the linear actuator, the end portion projecting from the casing to outside.

* * * * *